(12) United States Patent
Curran et al.

(10) Patent No.: US 7,364,908 B2
(45) Date of Patent: Apr. 29, 2008

(54) SEPARATION OF FLUOROUS COMPOUNDS

(75) Inventors: Dennis P. Curran, Pittsburgh, PA (US);
Masato Matsugi, Pittsburgh, PA (US);
Marvin S. Yu, Pittsburgh, PA (US)

(73) Assignees: University of Pittsburgh - Of the Commonwealth System of Higher Education, Pittsburgh, PA (US);
Fluorous Technologies Inc., Pittsburgh, PA (US)

( * ) Notice: Subject to any disclaimer, the term of this patent is extended or adjusted under 35 U.S.C. 154(b) by 399 days.

(21) Appl. No.: 10/870,514

(22) Filed: Jun. 17, 2004

(65) Prior Publication Data

US 2005/0283032 A1   Dec. 22, 2005

(51) Int. Cl.
G01N 37/00 (2006.01)
G01N 33/22 (2006.01)
C07C 19/08 (2006.01)
C07C 17/266 (2006.01)

(52) U.S. Cl. ........................ 436/56; 436/124; 570/142; 570/171; 570/177

(58) Field of Classification Search ................. 436/56, 436/124; 570/142, 171, 177
See application file for complete search history.

(56) References Cited

U.S. PATENT DOCUMENTS

| | | | |
|---|---|---|---|
| 4,735,848 A | 4/1988 | Kondo | |
| 5,777,121 A | 7/1998 | Curran | |
| 5,824,225 A | 10/1998 | Powell | |
| 5,859,247 A | 1/1999 | Curran | |
| 5,968,368 A | 10/1999 | Powell | |
| 6,156,896 A | 12/2000 | Curran | |
| 6,727,390 B2 | 4/2004 | Curran | |
| 6,734,318 B2 | 5/2004 | Curran | |
| 6,749,756 B1 | 6/2004 | Curran | |
| 6,806,357 B1 | 10/2004 | Curran | |
| 6,825,043 B1 * | 11/2004 | Curran et al. | 436/56 |
| 6,861,544 B1 | 3/2005 | Curran | |
| 6,897,331 B2 | 5/2005 | Curran | |
| 2004/0049071 A1 | 3/2004 | Curran | |
| 2004/0058948 A1 | 3/2004 | Curran | |
| 2004/0077674 A1 | 4/2004 | Curran | |
| 2004/0127755 A1 | 7/2004 | Gladysz | |
| 2004/0197829 A1 | 10/2004 | Curran | |

FOREIGN PATENT DOCUMENTS

EP   0 538 827   4/1993
EP   0 538 828   4/1993

OTHER PUBLICATIONS

Curran, J Org Chem, vol. 62, pp. 6714-6715, 1997.*
Matsuzawa, Hiroshi et. al. Highly Efficient Discrimination of Fluorous Tags by beta-Cyclodextrin Colunms: New Isolation Method for Fluorous Mixture Synthesis, Synlett 2000, No. 10, pp. 1607-1612.

Zhang, W.; Fluorous Technologies fro Solution-Phase High-Throughput Organic Synthesis; Tetrahedron 2003, 59, 4475-4489.

Barthel-Rosa, Luis P et al.; Chemistry in Fluorous Media: A User's Guide to Practical Consideration in the Application of Fluorous Catalysts and Reagents; Coord. Chem. Rev. 1999, 190-192, 587-605.

Curran, D. P.; Fluorous Reverse Phase Silica Gel. A New Tool for Preparative Separations in Synthetic Organic and Organofluorine Chemistry; Synlett 2001; No. 9; 1488-1496.

Dobbs, Adrian P., et al.; Fluorous Phase Chemistry: A New Industrial Technology; J. Fluorine Chem.; 2002; 118; 3-17.

Curran, Dennis P. et al.; Thermal Allylations of Aldehydes with a Fluorous Allylstannane. Separation of Organic and Fluorous Products by SOlid Phase EXtraction with Fluorous Reverse Phase Silica GEI; . J. Org. Chem. 1997, 62, 6714-6715.

Zhang, Qisheng, et al.; Separation of "Light Fluorous" Reagents and Catalysts by Fluorous Solid-Phase Extraction: Synthesis and Study of a Family of Triarylphosphines Bearing Linear and Branched Fluorous Tags; J. Org. Chem. 2000, 65, 8866-8873.

Attaway, John A.; Fluorocarbons as Solvents for Thin-Layer Chromatographic Analysis; Journal of Chromatography 1967, 31, 231-3.

Kagan, M. Z. Kagan; Normal-Phase High-Performance Liquid Chromatographic Separations Using Ethoxynonafluorobutane as Hexane Alternative I. Analytical and Chiral Applications; Journal of Chromatography A; 2001, 918, pp. 293-302.

Blackwell, J. A.; et al.; Hydrofluorocarbon and Perfluorocarbon Mobile Phases for Capillary Supercritical Fluid Chromatography, J. Microcol; Sep. 6, 1994, pp. 551-556.

Umemoto, Teruo, et al.; Reactions of Rfl(Ph)OSO2CF3 with Alkenes and Alkadienes; Tetrahedron Lett. 1982, 23, 1169-1172.

Matsuzawa, Hiroshi et al.; Efficient Enantiomeric Resolution Via Introduction of a Fluorous Tag as a Resolving Reagent with Beta-cyclodextrin Columns: Model Study on Fluorinated O-acetylmandelate and Ibuprofen Amide; Tetrahedron Letters 44 (2003), pp. 6227-6230.

(Continued)

Primary Examiner—D. Margaret Seaman
(74) Attorney, Agent, or Firm—Bartony & Hare, LLP

(57) ABSTRACT

A method of separating at least a first non-fluorous compound from a mixture of compounds including at least the first non-fluorous compound and a second fluorous compound includes: charging the of compounds to a non-fluorous solid (stationary) phase and eluting with a fluorous eluting fluid (mobile phase). In one embodiment, the non-fluorous solid phase is polar in nature. The method can further include a second phase elution with a suitable organic solvent. A method conducting a chemical reaction, includes: mixing at least a first fluorous compound and a second compound, the first fluorous compound differing in fluorous nature from the second compound; exposing the first mixture to conditions to convert at least one of the first fluorous compound and the second compound to give a second mixture containing at least a third compound, charging the second mixture to a non-fluorous solid phase; and eluting with a fluorous fluid.

15 Claims, 3 Drawing Sheets

OTHER PUBLICATIONS

Ryu, Ilhyong et al.; Synthesis of Perfluorinated Allylic Compounds by Radical Allylation and their Purification Over Fluorous Reverse-Phase Silica; Tetrahedron Lett. 2001, 42, 947-950.

Naji, N. et al; Synthese d'isoxazolines et d'isoxazoles F-alkyles en Milieu biphasique CHCL3-NaOCI; J. Fluorine Chem. 1996, 79, 179-183.

Mukaiyama, Teruaki, et al.; Peptide Synthesis via the Oxidation-Reduction COndensation by the Use of 2,2'-Dypyridyldisulfide as an Oxidant; Tetrahedron Lett. 1970, 22, 1901-1904.

Luo, Zhiyong, et al.; Fluorous Boc (FBOC) Carbamates: New Amine Protecting Groups for Use in Fluorous Synthesis; J. Org. Chem. 2001, 66, 4261-4266.

Tabuchi, Seiichiro, et al.; Novel Potent Antagonists of Human Neuropeptide Y Y5 Receptor. Part 1: 2-Oxobenzothiazolin-3-Acetic Acid Derivatives; Bio. & Med. Chem. Lett. 2002, 12, 1171-1175.

Keck, Gary E., et al.; One Electron C-C Bond Forming Reactions Via Allylstannanes: Scope and Limitations; Tetrahedron, 1985, 41, 4079-4094.

Tanaka, Hideo, et al.; Mg/PbBr2 Bimetal Redox-Promoted Stannation of Propargyl, Allyl, Vinyl and Aryl Halides; Synlett, 1993, 835-836.

Curran, D. P. In Stimulating Concepts in Chemistry. Fluorous Techniques for the Synthesis of Organic Molecules: A Unified Strategy for Reaction and Separation; Vögtle, F., Stoddardt, J. F., Shibasaki, M., Eds.; Wiley-VCH: New York, 2000.

* cited by examiner

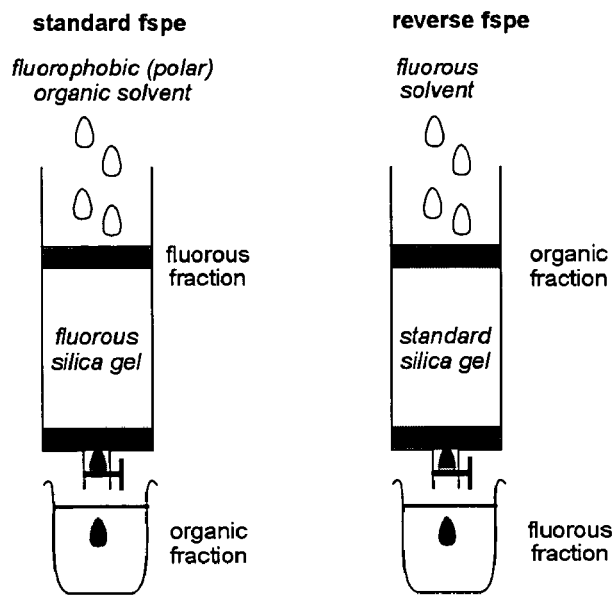
Fig. 1A PRIOR ART
Fig. 1B
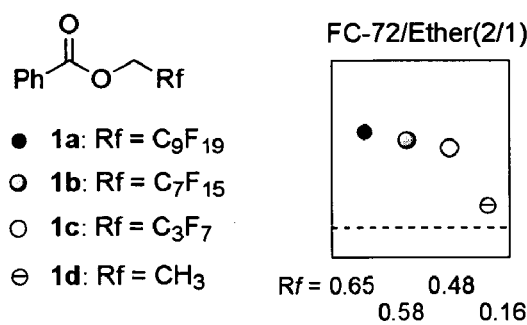
Fig. 2
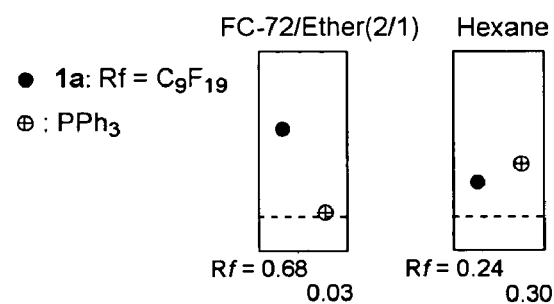
Fig. 3

| allyl stannane \ Rfl | $C_8F_{17}I$ | $C_{10}F_{21}I$ | $C_{12}F_{25}I$ | $(CF_3)_2CF(CF_2)_6I$ |
|---|---|---|---|---|
| ⟍⟋SnBu₃ (1 mmol scale) | $C_8F_{17}$⟍⟋ 2a, 82% | $C_{10}F_{21}$⟍⟋ 2b, 97% | $C_{12}F_{25}$⟍⟋ 2c, 89% | $(CF_3)_2CF(CF_2)_6$⟍⟋ 2d, 86% |
| Me ⟍⟋SnBu₃ (1 mmol scale) | $C_8F_{17}$⟍⟋Me 3a, 69% | $C_{10}F_{21}$⟍⟋Me 3b, 89% | $C_{12}F_{25}$⟍⟋Me 3c, 75% | $(CF_3)_2CF(CF_2)_6$⟍⟋Me 3d, 84% |
| Ph ⟍⟋SnBu₃ (0.4 mmol scale) | $C_8F_{17}$⟍⟋Ph 4a, 93% | $C_{10}F_{21}$⟍⟋Ph 4b, 90% | $C_{12}F_{25}$⟍⟋Ph 4c, 90% | $(CF_3)_2CF(CF_2)_6$⟍⟋Ph 4d, 86% |

SEPARATION OF FLUOROUS COMPOUNDS

GOVERNMENTAL RIGHTS

This invention was made with government support under grant RO1 GM033372 awarded by the National Institutes of Health. The government has certain rights in this invention.

BACKGROUND OF THE INVENTION

The present invention relates generally to separation of compounds and, particularly, to separation of compounds based upon differences in the fluorous nature of the compounds.

References set forth herein may facilitate understanding of the present invention or the background of the present invention. Inclusion of a reference herein, however, is not intended to and does not constitute an admission that the reference is available as prior art with respect to the present invention.

The separation of fluorous compounds from non-fluorous, organic compounds and/or from other fluorous compounds having a different fluorous nature is increasingly popular. Various fluorous separation techniques or methods are used to separate mixtures containing, for example, organic molecules and one or more fluorous molecules (organic molecules bearing fluorous domains or tags) from each other based predominantly on the fluorous nature of molecules (for example, the absence of a fluorous domain, the size of a fluorous domain and/or structure of a fluorous domain or molecule). In general, differences in the fluorous nature of molecules affect the interaction of the molecules with a "fluorophilic" or fluorous phase in the fluorous separation method. Early fluorous separation methods based on liquid-liquid separations have been augmented by solid-liquid separations like fluorous solid phase extraction (FSPE) and fluorous chromatography. See, for example, Zhang, W. *Tetrahedron* 2003, 59, 4475-4489; Curran, D. P. In *Stimulating Concepts in Chemistry*; Vögtle, F., Stoddardt, J. F., Shibasaki, M., Eds.; Wiley-VCH: New York, 2000; Dobbs, A. P.; Kimberley, M. R. *J. Fluorine Chem.* 2002, 118, 3-17; Barthel-Rosa, L. P.; Gladysz, J. A. *Coord. Chem. Rev.* 1999, 192, 587-605; Curran, D. P. Synlett 2001, 1488-1496; and U.S. Pat. Nos. 6,734,318, 6,727,390. 6,156,896, 5,859,247, and 5,777,121. Most of these types of separations rely on a fluorous silica solid phase (silica gel with a fluorocarbon bonded phase) coupled with an organic solvent.

Since their introduction in 1997, standard fluorous solid phase extractions have proven broadly useful for separating light fluorous molecules from organic molecules. See, for example, Curran, D. P.; Hadida, S.; He, M. *J. Org. Chem.* 1997, 62, 6714-6715; Zhang, Q.; Luo, Z.; Curran, D. P. *J. Org. Chem.* 2000, 65, 8866-8873. As illustrated in FIG. 1A, in a standard fluorous solid phase extraction to separate organic and fluorous compounds, a mixture of organic and fluorous compounds is loaded onto a "fluorophilic" (fluorous) silica gel followed by first pass elution with a "fluorophobic" (non-fluorous) solvent. Polar organic solvents (for example, 80-100% aqueous methanol or acetonitrile) are the most common fluorophobic solvents. During this first elution, the non-tagged organic compound is rapidly washed from the column while the fluorous-tagged compound is retained. A second pass elution (not shown) with a "fluorophilic" solvent (often $Et_2O$ or THF) then washes the fluorous fraction from the column.

Fluorous solvents or fluorous eluting fluids also have been used in connection with non-fluorous stationary phases in chromatographic separations of organic, non-fluorous compounds. See, for example, U.S. Pat. Nos. 5,824,225 and 5,968,368, J. A. Attaway, *Journal of Chromatography* 1967, 31, 231-3; M. Z. Kagan, *Journal of Chromatography, A* 2001, 918, 293-302; and J. A. Blackwell, L. E. Schallinger, *Journal of Microcolumn Separations* 1994, 6, 551-6. U.S. Pat. No. 5,824,225 indicates, for example, that use of using low boiling point (hydro)fluorocarbons and (hydro)fluorocarbon ethers as eluting fluids can facilitate removal of such solvents from the compounds which they elute.

Fluorinated eluting fluids have also been used to separate highly fluorinated macromolecules including hydroxyl end groups in silica gel columns. In that regard, European Patent Nos. 538827 and 538828 disclose the chromatographic separation of macromolecular mixtures of perfluoro polyoxyalkylenes in columns containing a stationary phase bearing polar groups able to bond with the hydroxyl end groups of the polymers (for example, a silica gel) using nonpolar fluorinated solvents (for example, 1,1,2,-trichloro-1,2,2-trifluoroethane) as elution agents.

Matsuzawa and Mikami have shown that cyclodextrins form inclusion complexes with fluorous compounds and separated a fluorinated ester ($C_6H_5CO_2CH_2Rf$) tagged with different perfluoroalkyl tags Rf (that is, —$CF_3$, —$C_2F_5$, —$C_3F_7$, —$C_7F_{15}$ or —$C_9F_{19}$) using HPLC columns packed with β- or γ-cyclodextrins. H. Matsuzawa, K. Mikami, *Synlett* 2002, 1607-12. In general, the separation tagged compounds synthesized by tagging a single organic compound with tags of differing nature can be effected by many separation techniques and is of little interest. The inclusion complexes formed between cyclodextrins and fluorous compound may result in an HPLC column packed with cyclodextrins bound to silica gel operating similarly to a column packed with fluorous silica gel as the cyclodextrins complex with fluorous solvents used in a separation.

Given the increasing utility and popularity of separations of a wide variety of mixtures of organic compounds based upon differences in fluorous nature, it is desirable to develop additional fluorous separation methods through which different organic compounds can be separated based upon differences in a fluorous nature thereof.

SUMMARY OF THE INVENTION

In one aspect, the present invention provides a method or separating at least a first non-fluorous compound from a mixture of compounds including at least the first non-fluorous compound and a second fluorous compound. The method includes charging the of compounds to a non-fluorous solid (stationary) phase and eluting with a fluorous eluting fluid (mobile phase). In one embodiment, the non-fluorous solid phase is polar in nature. The method can further include a second phase elution with a suitable organic solvent.

No complexing agent such as cyclodextrin is required in the stationary phase to form a complex with the fluorous compound(s) in the mixture.

In another aspect, the present invention provides a method of conducting a chemical reaction, including: mixing at least a first fluorous compound and a second compound, the first fluorous compound differing in fluorous nature from the second compound; exposing the first mixture conditions to convert at least one of the first fluorous compound and the second compound to give a second mixture containing at least a third compound, charging the second mixture to a non-fluorous solid phase; and eluting with a fluorous fluid.

In another aspect, the present invention provides a method of separating a first organic compound from a mixture comprising at least a second organic compound. The method includes the steps of: selectively reacting the first organic compound with a fluorous reaction component to attach a fluorous moiety to the first organic compound to result in a fluorous compound; and separating the fluorous compound from the second organic compound by charging the mixture to a non-fluorous solid phase and eluting with a fluorous fluid.

In a further aspect, the present invention provides a method of synthesizing an organic target product including the steps of: reacting a first organic compound with a first fluorous reaction component to attach a fluorous moiety to the first organic compound to result in a second fluorous reaction component; reacting the second fluorous reaction component in a reaction scheme including at least one reaction with at least a second organic compound to produce a fluorous target product in a reaction mixture; and separating the fluorous target product from any excess second organic compound and any organic byproduct by charging the reaction mixture to a non-fluorous solid phase and eluting with a fluorous fluid. The method can further include the step of reacting the fluorous target product to cleave the fluorous moiety and generate the organic target product.

In another aspect, the present invention provides a method of separating compounds including the steps of: tagging at least a first organic compound with a first fluorous tagging moiety to result in a first fluorous tagged compound; tagging at least a second organic compound with a second fluorous tagging moiety different from the first tagging moiety to result in a second fluorous tagged compound; and separating the first fluorous tagged compound from a mixture including the second fluorous tagged compound by charging the mixture to a non-fluorous solid phase and eluting with a fluorous fluid.

In another aspect, the present invention provides a method of physically separating compounds including the steps of: tagging at least a first organic compound with a first fluorous tagging moiety to result in a first fluorous tagged compound; tagging at least a second organic compound with a second fluorous tagging moiety different from the first fluorous tagging moiety to result in a second fluorous tagged compound; and physically separating the first tagged compound from a mixture including the second fluorous tagged compound by charging the mixture to a non-fluorous solid phase and eluting with a fluorous fluid.

In a further aspect, the present invention provides a method of physically separating compounds including the steps of: tagging a plurality of organic compounds with a plurality of fluorous tagging moieties to result in a plurality of fluorous tagged compounds, each of the fluorous tagging moieties being different; and physically separating at least one of the plurality of fluorous tagged compounds from other fluorous tagged compounds with a different tag by charging a mixture of the fluorous tagged compounds to a non-fluorous solid phase and eluting with a fluorous fluid.

In still a further aspect, the present invention provides a method for carrying out a chemical reaction including the steps of: tagging a plurality of compounds with different fluorous tagging moieties to create fluorous tagged compounds, conducting at least one chemical reaction on the fluorous tagged compounds to produce a mixture of fluorous tagged products, and separating at least one of the fluorous tagged products from the mixture of fluorous tagged products by charging the mixture to a non-fluorous solid phase and eluting with a fluorous fluid.

The fluorous eluting fluid of the present invention can, for example, be an individual fluorous fluid or a mixture of fluorous fluids. Many fluorous solvents are commercially available and include perfluoroalkanes (for example, perfluorohexane, perfluoromethylcyclohexane), perfluoroethers (for example, perfluorobutyltetrahydrofuran), perfluoroamines (for example, perfluorotributyl amine). Many fluorous solvents and fluids are performance fluid mixtures sold under trade names like FLUORINERT® (for example, FC-72, FC-75, etc.) available from Minnesota Mining and Manufacturing Company of Saint Paul, Minn., FLUTEC™ available from F2 Chemicals Ltd. of Lancashire, United Kingdom, and GALDEN® available from Ausimont S.P.A. of Milan, Italy. Examples and descriptions of representative fluorous solvents can be found in L. P. Barthel-Rosa, J. A. Gladysz, *Coord. Chem. Rev.* 1999, 192, 587-605, the disclosure of which is incorporated herein by reference. Also useful are highly fluorinated hydrocarbons, ethers (for example, perfluorobutyl ethyl ether), amines, halides (for example, perfluorooctyl bromide, referred to as "Oxygent"). Individual fluorous fluids or mixtures of fluorous fluids are preferentially more than 50% fluorine by molecular weight (as determined by a weighted average of the individual components of the fluid), and more preferentially are more than 60% percent fluorine by molecular weight.

The fluorous eluting fluid can also be an individual fluorous fluid or a mixture of fluorous fluids along with a cosolvent or a mixture of cosolvents. The cosolvents are selected from highly polar fluorous solvents (acids, alcohols), hybrid solvents, or organic solvents. The purpose of the cosolvent is to modify the Rf of one of more of the components being separated without substantially changing the fluorous nature of the separation. Generally, fluorous solvents are very non-polar, so one of the functions of the cosolvent is to increase the Rf of one or more components of the mixture on the non-fluorous solid phase. Therefore, the cosolvents are typically more polar than the fluorous solvent. Polar fluorinated alcohols (for example, 2,2,2-trifluoroethanol and 1,1,1,3,3,3-hexafluoroisopropanol), acids (for example trifluoroacetic acid and pentafluoropriopionic acid) and related fluorinated polar molecules are useful cosolvents. Also useful are other so-called "hybrid" (sometimes called "amphiphilc") solvents like benzotrifluoride and 1,1,2-trichloro-1,2,2,-trifluoroethane. Liquid or supercritical carbon dioxide can also be used as cosolvents. Also useful are conventional organic solvents. Preferred organic solvents include non-polar or moderately polar solvents like ethers (for example, diethyl ether, tetrahydrofuran), hydrocarbons (for example, hexane, toluene), and chlorocarbons (for example, dichloromethane). The preferred amount of cosolvent(s) is less than 50 volume % relative to the fluorous solvent(s), and the more preferred amount is less than 40 volume %. The fluorous eluting fluid should generally be a single fluid phase, and in many cases, the amount of organic solvent is limited by its miscibity in the fluorous fluid. Polar organic solvents (for example, DMF, methanol, acetonitrile, DMSO) are less preferred because they cause large increases in Rf of many compounds on polar non-fluorous stationary phases and because they have low solubilities in many fluorous fluids. However, they can be used in small amounts for some separations (typically, less than 5 volume %). Water can also be used in small amounts on occasion (typically less than 5 volume %). For example, cosolvents are generally used from commercial sources and special precautions for drying are not needed.

Preferred non-fluorous solid phases of the current invention are polar and are selected from an array of common chromatographic stationary phases. Many porous or mesoporous inorganic oxides or polymers, or bonded phases thereof, are useful. Examples of typical non-fluorous solid phases include silica gel (sold in many forms under many names), alumina (sometimes called aluminum oxide), titania, or zirconia. Polar bonded phases of silica gel and related media are also useful Such bonded phases include a plethora of polar groups including, for example, hydroxy groups, amino groups, ammonium groups, sulfonate groups, carboxylate groups and nitrile groups. Common chiral stationary phases such as Whelk-O and like phases available from Regis Technologies, Inc. of Morton Grove, Ill. and the CHIRALCEL phases available from Daicel Chemical Industries, Ltd. of Osaka, Japan, are also useful. Less preferred, but occasionally useful, stationary phases include non-polar bonded phases of silica gel such as reverse phase silica gel with a hydrocarbon bonded phase. Stationary phases with fluorous nature (for example, fluorous silica gel) are generally not desirable for use in the present invention.

As used herein, the term "fluorous", when used in connection with an organic (carbon-containing) molecule, moiety or group, refers generally to an organic molecule, moiety or group having a domain or a portion thereof rich in carbon-fluorine bonds (for example, fluorocarbons, fluorohydrocarbons, fluorinated ethers and fluorinated amines). As used herein, the term "perfluorocarbons" refers generally to organic compounds in which all hydrogen atoms bonded to carbon atoms have been replaced by fluorine atoms. The terms "fluorohydrocarbons" and "hydrofluorocarbons" include organic compounds in which at least one hydrogen atom bonded to a carbon atom has been replaced by a fluorine atom. Preferred fluorohydrocarbons and fluorohydrocarbon groups for use in the present invention have approximately two or more fluorines for every hydrogen. The attachment of fluorous moieties to organic compounds is discussed in U.S. Pat. Nos. 6,734,318, 6,727,390. 6,156,896, 5,859,247, and 5,777,121, the disclosures of which are incorporated herein by reference.

As used herein, the term "fluorous tagging" refers generally to attaching a fluorous moiety or group (referred to as a "fluorous tagging moiety" or "fluorous tagging group") to a compound to create a "fluorous tagged compound". Preferably, the fluorous tagging moiety is attached via covalent bond. However, other strong attachments such as ionic bonding or chelation can also be used. Fluorous tagging moieties used in certain embodiments of the reverse fluorous solid phase extraction separations of the present invention can be fluorous moieties that differ in fluorous nature (for example, fluorine content, size of the fluorous domain and/or structure of the fluorous domain). In certain cases, the fluorous tagging moieties are protecting groups.

As used herein, the term "solid phase extraction" (spe) refers generally to a liquid-solid separation technique in which a mixture of compounds is charged to a solid stationary phase. The charged mixture is then eluted with a fluid (for example, a solvent or mixture of solvents). One or several components of the mixture are eluted from the solid phase while another component or components is/are retained.

Further elutions with different liquids are sometimes conducted to elute additional components. While the reverse fluorous technique of the present invention is described generally in a solid phase extraction setting, it is clear to those skilled in the art that it is equally applicable to substantially any type of liquid-solid chromatography that uses a non-fluorous stationary phase. Examples include, but are not limited to, column chromatography, flash chromatography, paper chromatography, thin layer chromatography, medium pressure liquid chromatograhy (mplc), and high performance/pressure liquid chromatography (hplc). These and other common techniques are described, for example, in *Chemical Separations* by C. Meloan (Wiley-Interscence, 1999) and *The Essence of Chromatograpy* by C. F. Poole (Elsevier, 2003), the disclosures of which are incorporated herein by reference.

BRIEF DESCRIPTION OF THE DRAWINGS

The present invention, along with the attributes and attendant advantages thereof, will best be appreciated and understood in view of the following detailed description taken in conjunction with the accompanying drawings.

FIG. 1A illustrates a currently practiced or standard fluorous solid phase extraction.

FIG. 1B illustrates an embodiment of a reverse fluorous solid phase extraction of the present invention.

FIG. 2 illustrates a thin layer chromatographic separation of fluorous esters using a reverse fluorous solid phase extraction of the present invention.

FIG. 3 illustrates a comparison between results of a thin layer chromatographic separation using reverse fluorous conditions of the present invention and standard conditions.

DETAILED DESCRIPTION OF THE INVENTION

Figure 7:
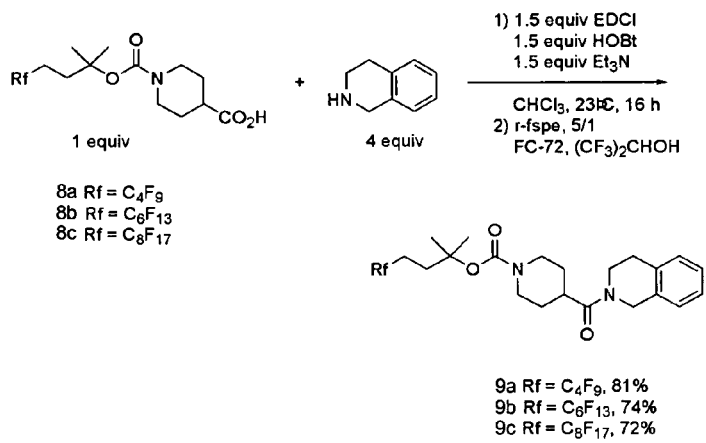
FIG. 7 illustrates isolation of F-Boc amides via reverse fluorous solid phase extraction.

In the fluorous separation techniques of the present invention, the solid, stationary phase has fluorophobic (non-fluorous) characteristics, while the liquid, mobile phase has fluorophilic (fluorous) characteristics. In one embodiment as illustrated in FIG. 1B, reverse fluorous solid phase extraction involves charging of a mixture of, for example, organic and fluorous compounds (for example, fluorous-tagged compounds) to a non-fluorous, polar solid phase. First pass elution with a fluorous liquid phase elutes the fluorous fraction from the column while leaving the organic fraction behind. If desired, second phase elution with a suitable organic solvent can elute the organic fraction.

Since fluorous solvents have been used only in a limited fashion in chromatographic processes, we first performed simple thin layer chromatographic (TLC) experiments with fluorous esters 1*a-d* to evaluate solvent and solid phase pairings. Several combinations of TLC plates and various fluorous solvents were studied. TLC plates studied included regular silica gel (Silica Gel 60 $F_{254}$ available from MERCK), base-coated silica gel (NH-DM1020 available from Fuji Silysia Chemical Co. Ltd.), C18-silica gel (C18-Silica Gel 60 $F_{254}$ available from MERCK), aluminum oxide (Aluminum oxide 150 $F_{254}$ available from MERCK), and α-cellulose (AVICEL F Microcrystalline Cellulose available from ANALTECH). Fluorous solvents studied included FC-72 (a mixture of perfluorohexanes, $c\text{-}C_6F_{11}CF_3$, $C_4F_9OMe$, benzotrifluoride (BTF; $C_6H_5CF_3$) and hexafluoroisopropanol. We found, for example, that a combination of a regular silica gel with mixtures of FC-72/Et$_2$O or FC-72/hexafluoroisopropanol provided both good separations and convenient Rf values, and these combinations were used in subsequent studies. Rf is the chromatographic retention factor. In that regard, the retention factor Rf of a compound in TLC is defined as the distance traveled by the compound divided by the distance traveled by the solvent front. The retention factor Rf should not be confused with the chemical substituent designation Rf, discussed below, which represents a fluorous moiety or group (a perfluoroalkyl group in the studies of the present invention).

FIG. 2 shows the Rf's of fluorinated benzoate esters (1a-d) on a regular silica gel TLC plate eluted with 2/1 FC-72/Et$_2$O. As expected, the Rf's of the esters increased with their fluorine content. This is the reverse of their behavior on fluorous silica gel eluting with polar organic solvents. The fluorous esters 1a-c had significantly higher Rf's than the non-fluorous methyl ester 1d.

Control TLC experiments with standard organic solvents revealed the unique features of using the fluorous solvent mixture with standard silica gel (see FIG. 3). For example, elution of a mixture of fluorous ester 1a and triphenylphosphine on standard silica gel with 100% hexane showed that triphenylphosphine was the less polar of the two compounds (Rf's: PPh$_3$, 0.30; 1a, 0.24). Rf's in 100% hexane were variable, possibly as a result of the water content of the silica gel. However, the relative polarities were not variable. When the same mixture was eluted with 2/1 FC-72/Et$_2$O on a silica TLC plate, the Rf of 1a increased to 0.68 while the Rf of PPh$_3$ decreased dramatically to 0.03. This decrease reflects the "fluorophobicity" of triphenylphosphine, which has little or no solubility in FC-72. The separation provided by the fluorous solvents is unique and cannot be reproduced with the common organic solvents used in silica TLC and chromatography experiments.

We also studied preparative separations of mixtures of fluorous and organic compounds by reverse fluorous solid phase extraction. Ryu and coworkers described allylation of perfluoroalkyl iodides (RfI) with allyl stannanes to provide allyl perfluoroalkanes. Ryu, I.; Kreimerman, S.; Niguma, T.; Minakata, S.; Komatsu, M.; Luo, Z.; Curran, D. P. *Tetrahedron Lett.* 2001, 42, 947-950, the disclosures of which are incorporated herein by reference. In that work, the target allylated products (fluorous) were separated from the tin residues (organic) by standard fluorous solid phase extraction. We conducted a similar set of reactions with purification by reverse fluorous solid phase extraction. The results of twelve experiments are summarized in FIG. 4.

Figure 4:
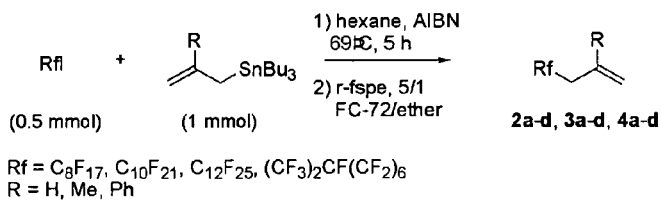
FIG. 4 illustrates result of preparation of 3-(perfluoroalkyl)prop-1-enes by reverse fluorous solid phase extraction.

In a typical procedure for reverse fluorous solid phase extraction in the studies of FIG. 4, a perfluoroalkyl iodide such as perfluorodecyl iodide (RfI, 323 mg, 0.5 mmol), allyltributyltin (330 mg, 1 mmol), AIBN (9 mg, 0.05 mmol) and hexane (5 ml) were placed in a flask under an argon atmosphere and the mixture was refluxed for 5 h. After removal of the volatile components by evaporation, the mixture was submitted to separation by reverse fluorous solid phase extraction. A short column was packed with regular silica gel (6.0 g) using FC-72/Et$_2$O (2/1) as the solvent. The crude reaction mixture was then loaded onto this column and eluted with 20 ml of FC-72/Et$_2$O (2/1) to give 3-(perfluorodecyl)prop-1-ene in 97% yield (271 mg). After similar reactions and separations, the allylated products 2a-d, 3a-d and 4a-d were isolated in yields ranging from 69-93%. The nuclear magnetic resonance (NMR) spectra of these products were clean, and gas chromatography (GC) or high pressure liquid chromatography (HPLC) purities exceeded 90% in all cases. The purity of the products was determined by GC in the case of R=H or R=Me and HPLC (Nova Pak® Silica, UV detection at 254 nm) in the case of R=Ph.

Figure 5:
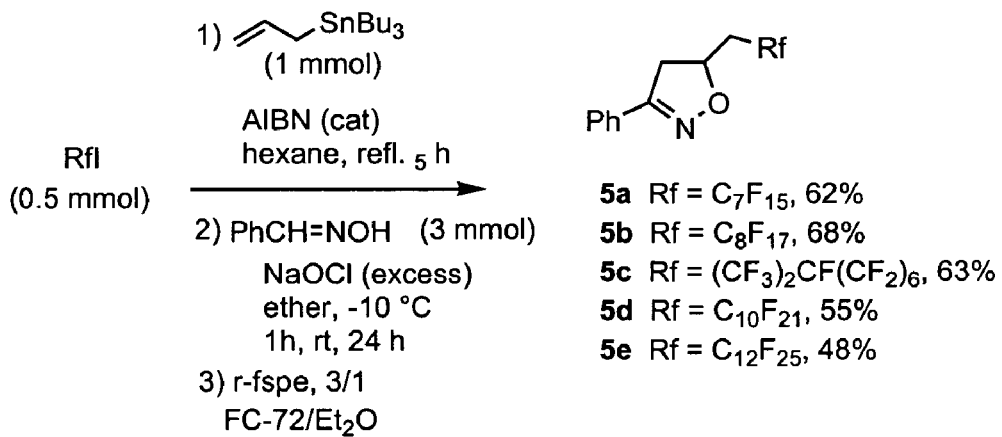
FIG. 5 illustrates the use of reverse fluorous solid phase extraction in connection with the multi-step sequence of allylation and nitrile oxide cycloaddition.

To show that reverse spe can be used to clean up multistep sequences, we conducted the sequence of allylation and nitrile oxide cycloaddition shown in FIG. 5. Five iodides were allylated as above and the crude products were directly subjected to nitrile oxide cycloaddition under oxidative conditions with excess benzaldehyde oxime. See Naji, N.; Soufiaoui, M.; Moreau, P. *J. Fluorine Chem.* 1996, 79, 179-183, the disclosure of which is incorporated herein by reference. TLC analysis of the crude products using standard organic solvents showed multiple spots and were suggestive of difficult chromatographic purifications. In contrast, TLC experiments with 2/1 FC-72/ether showed only a single spot (Rf~0.2) above the origin attributed to the target products. Reverse fluorous spe provided clean isoxazolines 5a-e in 48-68% yield.

Figure 6:
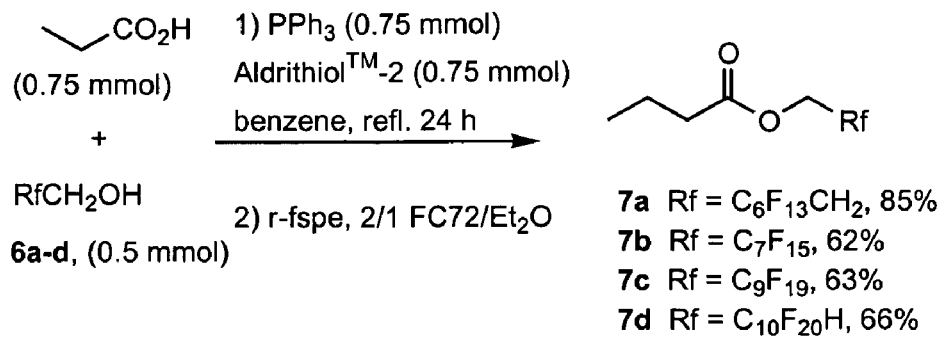
FIG. 6 illustrates the removal of triphenylphosphine and its derived oxide from perfluoroalkyl butyrates via by reverse fluorous solid phase extraction.

The TLC experiments in FIG. 3 suggest that reverse fluorous spe should be useful for removing triphenylphosphine and its derived oxide from fluorous compounds. To show this, we reacted limiting amounts of four fluorous alcohols 6a-d (0.5 mmol) with excess (0.75 mmol) butyric acid, triphenylphosphine, and Aldrichthiol™-2 (2,2-dipyridyl disulfide). See Mukaiyama, T.; Matsueda, R.; Suzuki, M. *Tetrahedron Lett.* 1970, 22, 1901-1904, the disclosure of which is incorporate herein by reference. Reaction for 24 h in refluxing benzene, followed by cooling and reverse fluorous solid phase extraction provided the products 7a-7d in 62-85% yield, free from reagents and reagent-derived byproducts (see FIG. 6).

We also applied the reverse fluorous solid phase extraction procedure to a standard amide coupling reaction of isonipecotic acid protected on nitrogen with three different fluorous Boc groups as illustrated in FIG. 7. Such reactions are described in Luo, Z.; Williams, J.; Read, R. W.; Curran, D. P. *J. Org. Chem.* 2001, 66, 4261-4266 and Tabuchi, S.; Itani, H.; Sakata, Y.; Oohashi, H.; Satoh, Y. *Bio. & Med. Chem. Lett.* 2002, 12, 1171-1175, the disclosures of which are incorporated herein by reference. Couplings of 8a-c (0.06 mmol) with excess tetrahydroisoquinoline (0.24 mol) were effected under standard conditions with EDCI, HOBt and Et$_3$N in CHCl$_3$ (1 mL). The mixtures were partially concentrated and charged to 1 g of silica gel. Elution with 5 mL FC-72/hexfluoroisopropanol (5/1) provided products 9a-c in 72-81% yield with hplc purities of 93-96%. The purity of the products was determined by HPLC (Nova Pak® Silica) with UV detection at 254 nm. Unreacted or spent reagent and reactant byproducts were not evident in the $^1$H NMR spectra of any of these products. The satisfactory result with the substrate 8a bearing the small C$_4$F$_9$ fluorous tag is especially noteworthy because these tags are normally considered too small for reliable separations by standard fluorous solid phase extraction. The relative polarities of the reagents and reactants may contribute to the success with 9a.

The reverse fluorous solid phase extraction methods of the present invention can readily use inexpensive silica gel along with fluorous solvents that are routinely recovered and recycled. Several useful solvent conditions are identified above, and these and others can readily be evaluated by simple thin layer chromatography (TLC) experiments. Because fluorous products elute first, the method is especially useful when the fluorous products are the target product of a given reaction. Fluorous products are the target products, for example, in fluorous tagging methods (such as illustrated, for example, in FIG. 7) and in the synthesis of highly fluorinated molecules (such as illustrated, for example, in FIG. 4). The reverse fluorous solid phase extraction can be aided by choosing organic components that are polar, since these are naturally better retained on silica gel. Extensions to flash chromatographic and HPLC separations are readily accomplished.

EXPERIMENTAL EXAMPLES

General: All melting points are uncorrected. Reagents were used as they were received from Aldrich. $^1$H and $^{19}$F NMR spectra were measured in $CDCl_3$ with TMS or $CHCl_3$ as the internal standard. 2-Methylallyltributyltin and 2-phenylallyltributyltin were prepared by known procedure. See Keck, G. E.; Enholm, E. J.; Yates, J. B.; Wiley, M. R. *Tetrahedron*, 1985, 41, 4079-4094 and Tanaka, H.; Hai, A. K. M. A.; Ogawa, H.; Torii, S. *Synlett*, 1993, 835-836, the disclosures of which are incorporated herein by reference. Fluorous benzoates 1a-c were prepared by condensation of the corresponding fluoroalcohols and benzoyl chloride. Fluorous alkenes 2a-b, 2d, 3a-b, 3d, 4a, fluorous ester 7c and fluorous amides 9c were known compounds. See Matsuzawa, H.; Mikami, K. *Synlett*, 2002, 1607-1612; Ryu, I.; Kreimerman, S.; Niguma, T.; Minakata, S.; Komatsu, M.; Luo, Z.; Curran, D. P. *Tetrahedron Lett*. 2001, 42, 947-950; Umemoto, T.; Kuriu, Y.; Nakayama, S. *Tetrahedron Lett*. 1982, 23, 1169-1172; Kondou, H.; Kawana, T.; Yatagai, H. Pat. Specif. (Aust.) (1989), 56 pp. CAN 112:170785; and Luo, Z.; Williams, J.; Read, R. W.; Curran, D. P. *J. Org. Chem*. 2001, 66, 4261-4266, the disclosures of which is incorporated herein by reference. The purities of 2a-d and 3a-d were determined by GC. The purities of 4a-d were determined by HPLC.

Benzoic acid 2,2,3,3,4,4,5,5,6,6,7,7,8,8,9,9,10,10,10-nonadecafluorodecyl ester 1a Colorless solid; mp 52.5-53.0° C.; $^1$H NMR (300 MHz, $CDCl_3$) δ 4.84 (t, 2H, J=13.3 Hz), 7.50 (t, 2H, J=7.9 Hz), 7.64 (t, 1H, J=7.9 Hz), 8.08 (d, 2H, J=7.2 Hz); $^{19}$F NMR (272 MHz, $CDCl_3$)-124.9 (2F), −121.9 (2F), −121.5 (2F), −120.6 (8F), −118.0 (2F), −79.5 (3F).

Benzoic acid 2,2,3,3,4,4,5,5,6,6,7,7,8,8-pentadecafluorooctyl ester 1b

Colorless oil; $^1$H NMR (300 MHz, $CDCl_3$) δ 4.84 (t, 2H, J=13.3 Hz), 7.50 (t, 2H, J=7.6 Hz), 7.64 (t, 1H, J=7.6 Hz), 8.08 (d, 2H, J=7.3 Hz); $^{19}$F NMR (272 MHz, $CDCl_3$) δ −124.9 (2F), −121.9 (2F), −121.5 (2F), −120.7 (4F), −118.0 (2F), −79.6 (3F).

Benzoic acid 2,2,3,3,4,4,4-heptafluorobutyl ester 1c

Colorless oil; $^1$H NMR (300 MHz, $CDCl_3$) δ 4.82 (t, 2H, J=13.2 Hz), 7.49 (t, 2H, J=7.5 Hz), 7.63 (t, 1H, J=7.5 Hz), 8.08 (d, 2H, J=7.4 Hz); $^{19}$F NMR (272 MHz, $CDCl_3$) δ −126.3 (2F), −119.1 (2F), −79.6 (3F).

Example 1

Typical procedure for a preparation of 3-(perfluoroalkyl) prop-1-enes by reverse fluorous solid phase extraction: Under argon atmosphere, perfluorooctyl iodide (272 mg, 0.5 mmol), tributylallylstannane (330 mg, 1.0 mmol) and AIBN (9 mg, 10 mol %) were dissolved in 5 mL of hexane. After stirring at 80° C. for 5 h, the reaction mixture was cooled, concentrated and charged to a column containing 6 g of standard silica gel. The column was eluted with 20 mL FC-72/diethylether (2/1), and the solvent was evaporated to provide the 2a (189 mg, 82%) as a colorless oil.

4,4,5,5,6,6,7,7,8,8,9,9,10,10,11,11,11-Heptadecafluoroundec-1-ene 2a

Colorless oil (82% yield, 95.1% GC purity); $^1$H NMR (300 MHz, $CDCl_3$) δ 2.86 (dt, 2H, J=18.2, 6.7 Hz), 5.35 (m, 2H), 5.80 (m, 2H); $^{19}$F NMR (272 MHz, $CDCl_3$) δ −125.2 (2F), −122.4 (2F), −121.9 (2F), −120.7 (6F), −112.1 (2F), −79.4 (3F).

4,4,5,5,6,6,7,7,8,8,9,9,10,10,11,11,12,12,13,13,13-Heneicosafluorotridec-1-ene 2b Colorless oil (97% yield, 97.0% purity); $^1$H NMR (300 MHz, $CDCl_3$) δ 2.86 (dt, 2H, J=18.2, 6.7 Hz), 5.36 (m, 2H), 5.81 (m, 2H); $^{19}$F NMR (272 MHz, $CDCl_3$) δ −124.8 (2F), −121.9 (2F), −121.6 (2F), −120.6 (10F), −112.1 (2F), −79.5 (3F).

4,4,5,5,6,6,7,7,8,8,9,9,10,10,11,11,12,12,13,13,14,14,15,15,15-Pentacosafluoropentadec-1-ene 2c Colorless solid (89% yield, 94.5% purity); mp 74.5-75.0° C.; $^1$H NMR (300 MHz, $CDCl_3$) δ 2.86 (dt, 2H, J=18.3, 6.9 Hz), 5.35 (m, 2H), 5.81 (m, 2H); $^{19}$F NMR (272 MHz, $CDCl_3$) δ −124.9 (2F), −121.9 (2F), −121.5 (2F), −120.5 (14F), −112.0 (2F), −79.5 (3F); HRMS (EI)

Calcd for $C_{15}H_5F_{25}$ (M$^+$): 659.9992. Found: 659.9996.

4,4,5,5,6,6,7,7,8,8,9,9,10,11,11,11-Hexadecafluoro-10-trifluoromethylundec-1-ene 2d Colorless oil (86% yield, 92.2% purity); $^1$H NMR (300 MHz, $CDCl_3$) δ 2.86 (dt, 2H, J=18.3, 6.9 Hz), 5.36 (m, 2H), 5.81 (m, 2H); $^{19}$F NMR (272 MHz, $CDCl_3$) δ 184.8 (1F), −121.9 (2F), −120.3 (4F), −119.6 (2F), −113.8 (2F), −112.1 (2F), −70.8 (6F).

4,4,5,5,6,6,7,7,8,8,9,9,10,10,11,11,11-Heptadecafluoro-2-methylundec-1-ene 3a

Colorless oil (69% yield, purity); $^1$H NMR (300 MHz, $CDCl_3$) δ 1.96 (s, 3H), 2.94 (t, 2H, J=19.1 Hz), 5.06 (s, 1H), 5.19 (s, 1H); $^{19}$F NMR (272 MHz, $CDCl_3$) δ −125.1 (2F), −122.2 (2F), −121.5 (2F), −120.7 (6F), −111.5 (2F), −79.5 (3F).

4,4,5,5,6,6,7,7,8,8,9,9,10,10,11,11,12,12,13,13,13-Heneicosafluoro-2-methyltridec-1-ene 3b Colorless solid (89% yield, 92.0% purity); mp 49.5-51.5° C.; $^1$H NMR (300 MHz, $CDCl_3$) δ 1.88 (s, 3H), 2.79 (t, 2H, J=19.4 Hz), 4.98 (s, 1H), 5.11 (s, 1H); $^{19}$F NMR (272 MHz, $CDCl_3$) δ −124.9 (2F), −122.0 (2F), −121.7 (2F), −120.6 (10F), −111.7 (2F), −79.5 (3F).

4,4,5,5,6,6,7,7,8,8,9,9,10,10,11,11,12,12,13,13,14,14,15,15,15-Pentacosafluoro-2-methylpentadec-1-ene 3c Colorless amorphous (75% yield, 91.3% purity); $^1$H NMR (300 MHz, $CDCl_3$) δ 1.88 (s, 3H), 2.79 (t, 2H, J=19.1

Hz), 4.98 (s, 1H), 5.11 (s, 1H); $^{19}$F NMR (272 MHz, CDCl$_3$) δ −124.8 (2F), −122.0 (2F), −121.5 (2F), −120.5 (14F), −111.5 (2F), −79.5 (3F).

4,4,5,5,6,6,7,7,8,8,9,9,10,11,11,11-Hexadecafluoro-2-methyl-10-trifluoromethylundec-1-ene 3d Colorless amorphous (84% yield, 92.0% purity); $^1$H NMR (300 MHz, CDCl$_3$) δ 1.88 (s, 3H), 2.79 (t, 2H, J=19.3 Hz), 4.97 (s, 1H), 5.11 (s, 1H); $^{19}$F NMR (272 MHz, CDCl$_3$) δ −185.0 (1F), −122.4 (2F), −120.5 (4F), −119.6 (2F), −113.9 (2F), −111.8 (2F), −70.8 (6F).

[1-(2,2,3,3,4,4,5,5,6,6,7,7,8,8,9,9,9-Heptadecafluorononyl)vinyl]benzene 4a

Colorless amorphous (93% yield, 97.5% purity); $^1$H NMR (300 MHz, CDCl$_3$) δ 3.29 (t, 2H, J=18.6 Hz), 5.39 (s, 1H), 5.65 (s, 1H), 7.29-7.42 (m, 5H); $^{19}$F NMR (272 MHz, CDCl$_3$) δ −124.9 (2F), −122.1 (2F), −121.5 (2F), −120.7 (4F), −120.4 (2F), −111.2 (2F), −79.5 (3F); HRMS (EI) Calcd for C$_{17}$H$_9$F$_{17}$ (M$^+$): 536.0432. Found: 536.0408.

[1-(2,2,3,3,4,4,5,5,6,6,7,7,8,8,9,9,10,10,11,11,11-Heneicosafluoroundecyl)vinyl]benzene 4b Colorless solid (93% yield, 97.5% purity); mp 57.0-58.0° C.; $^1$H NMR (300 MHz, CDCl$_3$) δ 3.30 (t, 2H, J=18.6 Hz), 5.39 (s, 1H), 5.65 (s, 1H), 7.27-7.43 (m, 5H); $^{19}$F NMR (272 MHz, CDCl$_3$) δ −125.3 (2F), −122.1 (2F), −121.5 (2F), −120.6 (10F), −111.2 (2F), −79.5 (3F); HRMS (EI) Calcd for C$_{19}$H$_9$F$_{21}$ (M$^+$): 636.0369. Found: 636.0344.

[1-(2,2,3,3,4,4,5,5,6,6,7,7,8,8,9,9,10,10,11,11,12,12,13,13,13-Pentacosafluorotridecyl)vinyl]benzene 4c Colorless solid (90% yield, 90.8% purity); mp 81.5-82.5° C.; $^1$H NMR (300 MHz, CDCl$_3$) δ 3.30 (t, 2H, J=18.7 Hz), 5.39 (s, 1H), 5.65 (s, 1H), 7.31-7.42 (m, 5H); $^{19}$F NMR (272 MHz, CDCl$_3$) δ −124.9 (2F), −122.4 (2F), −121.8 (2F), −120.5 (14F), −111.2 (2F), −79.5 (3F); HRMS (EI) Calcd for C$_{21}$H$_9$F$_{25}$ (M$^+$): 736.0305. Found: 736.0342.

[1-(2,2,3,3,4,4,5,5,6,6,7,7,8,9,9,9-Hexadecafluoro-8-trifluoromethylnonyl)vinyl]benzene 4d Colorless amorphous (86% yield, 99.4% purity); $^1$H NMR (300 MHz, CDCl$_3$) δ 3.29 (t, 2H, J=18.5 Hz), 5.39 (s, 1H), 5.65 (s, 1H), 7.29-7.43 (m, 5H); $^{19}$F NMR (272 MHz, CDCl$_3$) δ −184.9 (1F), −122.3 (2F), −120.3 (4F), −119.6 (2F), −113.8 (2F), −111.2 (2F), −70.7 (6F); HRMS (EI) Calcd for C$_{18}$H$_9$F$_{19}$ (M$^+$): 586.0401. Found: 586.0401.

Example 2

Typical procedure for a preparation of 5 by reverse fluorous solid phase extraction: Under argon atmosphere, perfluorooctyl iodide (272 mg, 0.5 mmol), tributylallylstannane (330 mg, 1.0 mmol) and AIBN (9 mg, 10 mol %) were dissolved in 5 mL of hexane. After stirring at 80° C. for 5 h, the reaction mixture was cooled, concentrated and added diethylether (10 ml). To the reaction mixture, benzaldehyde oxime (363 mg, 3.0 mmol) and sodium hypochlorite solution (10 ml, available chlorine 10-13%) were added at −10° C. and stirred vigorously at 23° C. for 24 h. After the organic layer was separated and concentrated in vacuo, the residue was charged to a column containing 8 g of standard silica gel. The column was eluted with 70 mL FC-72/diethylether (3/1), and the solvent was evaporated to provide the 5b (197 mg, 68%) as a colorless solid.

5-(2,2,3,3,4,4,5,5,6,6,7,7,8,8,8-Pentadecafluorooctyl)-3-phenyl-4,5-dihydro-isoxazole 5a Colorless solid (62% yield); mp 91.0-92.0° C.; $^1$H NMR (300 MHz, CDCl$_3$) δ 2.45 (m, 1H), 2.76 (m, 1H), 3.19 (m, 1H), 3.62 (m, 1H), 5.14 (m, 1H), 7.43 (m, 3H), 7.69 (dd, 2H, J=7.5, 1.9 Hz); $^{19}$F NMR (272 MHz, CDCl$_3$) δ −125.0 (2F), −122.3 (2F), −121.5 (2F), −120.9 (2F), −120.4 (2F), −111.4 (2F), −79.6 (3F); HRMS (EI) Calcd for C$_{17}$H$_{10}$F$_{15}$NO (M$^+$): 529.0520. Found: 529.0523.

5-(2,2,3,3,4,4,5,5,6,6,7,7,8,8,9,9,9-Heptadecafluorononyl)-3-phenyl-4,5-dihydroisoxazole 5b Colorless solid (68% yield); mp 100.5-101.0° C.; $^1$H NMR (300 MHz, CDCl$_3$) δ 2.45 (m, 1H), 2.78 (m, 1H), 3.22 (m, 1H), 3.60 (m, 1H), 5.11 (m, 1H), 7.44 (m, 3H), 7.69 (d, 2H, J=7.5 Hz); $^{19}$F NMR (272 MHz, CDCl$_3$) δ −124.9 (2F), −122.2 (2F), −121.5 (2F), −120.7 (4F), −120.4 (2F), −111.3 (2F), −79.5 (3F); $^{13}$C NMR (75 MHz, CDCl$_3$) δ 36.3, 41.0, 74.2, 105-120 (m, C$_8$F$_{17}$), 126.8, 129.0, 130.6, 156.8.

5-(2,2,3,3,4,4,5,5,6,6,7,7,8,9,9,9-Hexadecafluoro-8-trifluoromethylnonyl)-3-phenyl-4,5-dihydroisoxazole 5c Colorless solid (63% yield); mp 89.0-90.0° C.; $^1$H NMR (300 MHz, CDCl$_3$) δ 2.46 (m, 1H), 2.80 (m, 1H), 3.20 (m, 1H), 3.65 (m, 1H), 5.11 (m, 1H), 7.45 (m, 3H), 7.69 (m, 2H); $^{19}$F NMR (272 MHz, CDCl$_3$) δ −184.9 (1F), −122.2 (2F), −120.3 (4F), −119.5 (2F), −113.8 (2F), −111.4 (2F), −70.6 (6F); $^{13}$C NMR (75 MHz, CDCl$_3$) δ 36.2, 41.0, 74.2, 105-120 (m, C$_8$F$_{17}$), 126.8, 128.9, 130.6, 156.8; HRMS (EI) Calcd for C$_{19}$H$_{10}$F$_{19}$NO (M$^+$): 629.0486. Found: 629.0459.

5-(2,2,3,3,4,4,5,5,6,6,7,7,8,8,9,9,10,10,11,11,11-Heneicosafluoroundecyl)-3-phenyl-4,5-dihydroisoxazole 5d Colorless solid (55% yield); mp 120.0-121.0° C.; $^1$H NMR (300 MHz, CDCl$_3$) δ 2.46 (m, 1H), 2.80 (m, 1H), 3.20 (m, 1H), 3.60 (m, 1H), 5.10 (m, 1H), 7.44 (m, 3H), 7.68 (m, 2H); $^{19}$F NMR (272 MHz, CDCl$_3$) δ −124.9 (2F), −122.2 (2F), −121.5 (2F), −120.5 (10F), −111.4 (2F), −79.5 (3F); HRMS (EI) Calcd for C$_{20}$H$_{10}$F$_{21}$NO (M$^+$): 679.0452. Found: 679.0427.

5-(2,2,3,3,4,4,5,5,6,6,7,7,8,8,9,9,10,10,11,11,12,12,13,13,13-Pentacosafluorotridecyl)-3-phenyl-4,5-dihydroisoxazole 5e Colorless solid (55% yield); mp 144.0-144.5° C.; $^1$H NMR (300 MHz, CDCl$_3$) δ 2.45 (m, 1H), 2.79 (m, 1H), 3.20 (m, 1H), 3.61 (m, 1H), 5.11 (m, 1H), 7.44 (m, 3H), 7.69 (m, 2H); $^{19}$F NMR (272 MHz, CDCl$_3$) δ −124.9 (2F), −122.2 (2F), −121.5 (2F), −120.5 (14F), −111.3 (2F), −79.5 (3F); HRMS (EI) Calcd for C$_{22}$H$_{10}$F$_{25}$NO (M$^+$): 779.0359. Found: 779.0363.

Example 3

Typical procedure for a preparation of 7 by reverse fluorous solid phase extraction: Under argon atmosphere, 3,3,4,4,5,5,6,6,7,7,8,8,8-Tridecafluorooctan-1-ol 6a (182 mg, 0.5 mmol), butyric acid (66 mg, 0.75 mmol), triphenylphospine (197 mg, 0.75 mmol) and Aldrithiol™-2 (165 mg, 0.75 mmol) were dissolved in 5 mL of benzene. After stirring at 80° C. for 24 h, the reaction mixture was cooled, concentrated and charged to a column containing 6 g of standard silica gel. The column was eluted with 20 mL FC-72/diethylether (2/1), and the solvent was evaporated to provide the 7a (185 mg, 85%) as a colorless oil.

Butyric acid 3,3,4,4,5,5,6,6,7,7,8,8,8-tridecafluorooctyl ester 7a

Colorless oil (85% yield); $^1$H NMR (300 MHz, CDCl$_3$) δ 0.96 (t, 3H, J=7.4 Hz), 1.66 (m, 2H), 2.32 (t, 2H, J=7.4 Hz), 2.50 (m, 2H), 4.39 (t, 2H, J=6.5 Hz); $^{19}$F NMR (272 MHz, CDCl$_3$) δ −125.0 (2F), −122.4 (2F), −121.7 (2F), −120.7 (2F), −112.5 (2F), −79.5 (3F); HRMS (EI) Calcd for C$_{12}$H$_{11}$F$_{13}$O$_2$ (M$^+$): 434.0541. Found: 434.0551.

Butyric acid 2,2,3,3,4,4,5,5,6,6,7,7,8,8,8-pentadecafluorooctyl ester 7b

Colorless oil (62% yield); $^1$H NMR (300 MHz, CDCl$_3$) δ 0.98 (t, 3H, J=7.4 Hz), 1.67 (m, 2H), 2.41 (t, 2H, J=7.4 Hz), 4.60 (t, 2H, J=13.6 Hz); $^{19}$F NMR (272 MHz, CDCl$_3$) δ −124.9 (2F), −122.1 (2F), −121.5 (2F), −120.8 (4F), −118.3 (2F), −79.5 (3F); HRMS (EI) Calcd for C$_{12}$H$_9$F$_{15}$O$_2$ (M$^+$): 470.0383. Found: 470.0363.

Butyric acid 2,2,3,3,4,4,5,5,6,6,7,7,8,8,9,9,10,10,10-nonadecafluorodecyl ester 7c Colorless oil (63% yield); $^1$H NMR (300 MHz, CDCl$_3$) δ 0.98 (t, 3H, J=7.4 Hz), 1.67 (m, 2H), 2.41 (t, 2H, J=7.4 Hz), 4.60 (t, 2H, J=13.6 Hz); $^{19}$F NMR (272 MHz, CDCl$_3$) δ −124.9 (2F), −122.1 (2F), −121.5 (2F), −120.7 (8F), −118.3 (2F), −79.5 (3F).

Butyric acid 2,2,3,3,4,4,5,5,6,6,7,7,8,8,9,9,10,10,11,11-eicosafluoroundecyl ester 7d Colorless solid (66% yield); mp 32.0-33.0° C.; $^1$H NMR (300 MHz, CDCl$_3$) δ 0.98 (t, 3H, J=7.4 Hz), 1.70 (m, 2H), 4.60 (t, 2H, J=13.7 Hz), 6.07 (m, 1H); $^{19}$F NMR (272 MHz, CDCl$_3$) δ −135.8 (2F), −128.0 (2F), −122.1 (4F), −120.6 (10F), −118.3 (2F); HRMS (EI) Calcd for C$_{15}$H$_{10}$F$_{20}$O$_2$ (M$^+$): 602.0369. Found: 602.0361.

Example 4

Typical procedure for a preparation of 9 by reverse fluorous solid phase extraction: Under argon atmosphere, piperidine-1,4-dicarboxylic acid mono(4,4,5,5,6,6,7,7,7-nonafluoro-1,1-dimethylheptyl) ester 8a (27.7 mg, 0.06 mmol), EDCI (17.3 mg, 0.09 mmol), HOBT (12.2 mg, 0.09 mmol) and triethylamine (12.5 μl, 0.09 mmol) were dissolved in 1 mL of chloroform. After stirring at 23° C. for 16 h, the reaction mixture was concentrated and charged to a column containing 1 g of standard silica gel. The column was eluted with 5 mL FC-72/hexafluoroisopropanol (5/1), and the solvent was evaporated to provide the 9a (27.0 mg, 81%) as a colorless solid.

4-(3,4-Dihydro-1H-isoquinoline-2-carbonyl)piperidine-1-carboxylic acid 4,4,5,5,6,6,7,7,7-nonafluoro-1,1-dimethylheptyl ester 9a Colorless solid (81% yield, 96.0% purity); mp 83.5-84.0° C.; $^1$H NMR (300 MHz, CDCl$_3$) δ 1.55 (s, 6H), 1.74 (bs, 4H), 2.05-2.18 (m, 4H), 2.78-3.00 (m, 5H), 3.74 (t, 1H, J=5.9 Hz), 3.84 (bs, 1H), 4.15 (m, 2H), 4.69 (s, 1H), 4.71 (s, 1H), 7.15-7.27 (m, 4H); $^{19}$F NMR (272 MHz, CDCl$_3$) δ −124.8 (2F), −123.0 (2F), −113.3 (2F), −79.8 (3F).

4-(3,4-Dihydro-1H-isoquinoline-2-carbonyl)piperidine-1-carboxylic acid 4,4,5,5,6,6,7,7,8,8,9,9,9-tridecafluoro-1,1-dimethylnonyl ester 9b Colorless solid (74% yield, 96.2% purity); mp 97.0-97.5° C.; $^1$H NMR (300 MHz, CDCl$_3$) δ 1.51 (s, 6H), 1.74 (bs, 4H), 2.06-2.18 (m, 4H), 2.84-2.95 (m, 5H), 3.74 (t, 1H, J=5.9 Hz), 3.85 (bs, 1H), 4.16 (m, 2H), 4.69 (s, 1H), 4.71 (s, 1H), 7.17-7.27 (m, 4H); $^{19}$F NMR (272 MHz, CDCl$_3$) δ −124.9 (2F), −122.0 (2F), −121.6 (2F), −120.7 (2F), −113.1 (2F), −79.6 (3F).

4-(3,4-Dihydro-1H-isoquinoline-2-carbonyl)piperidine-1-carboxylic acid 4,4,5,5,6,6,7,7,8,8,9,9,10,10,11,11,11-heptadecafluoro-1,1-dimethyl-undecyl ester 9c Colorless solid (72% yield, 93.0% purity); mp 111.5-112.0° C.; $^1$H NMR (300 MHz, CDCl$_3$) δ 1.54 (s, 6H), 1.76 (bs, 4H), 2.19-2.25 (m, 4H), 2.80-3.00 (m, 5H), 3.74 (t, 1H, J=6.0 Hz), 3.85 (bs, 1H), 4.15 (m, 2H), 4.71 (s, 1H), 4.75 (s, 1H), 7.18-7.30 (m, 4H).

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A method or separating at least a first non-fluorous compound from a mixture of compounds including at least the first non-fluorous compound and a second fluorous compound; comprising:
charging the mixture of compounds to a non-fluorous solid phase and eluting with a fluorous eluting fluid.

2. The method of claim 1 wherein the non-fluorous solid phase is polar in nature.

3. The method of claim 2 wherein the non-fluorous solid phase is a silica gel.

4. The method of claim 1 wherein the non-fluorous solid phase comprises a porous inorganic oxide, a mesoporous inorganic oxide, a porous polymer, or a mesoporous polymer.

5. The method of claim 1 wherein the non-fluorous solid phase comprises silica gel, alumina, titania, or zirconia.

6. The method of claim 1 wherein the non-fluorous solid phase comprises a polar bonded phase of silica gel, alumina, titania, or zirconia.

7. The method of claim 1 wherein the non-fluorous solid phase comprises a nonpolar bonded phase of silica gel, alumina, titania, or zirconia.

8. The method of claim 1 wherein the non-fluorous solid phase comprises a chiral stationary phase.

9. The method of claim 1 further comprising a second phase elution with a suitable organic solvent.

10. The method of claim 1 wherein the fluorous eluting fluid comprises at least one of a fluorinated alkane, a fluorinated ether, or a fluorinated amine.

11. The method of claim 1 wherein the fluorous eluting fluid comprises at least one of a hydrofluoroalkane, a hydrofluoroether, a hydrofluoroamine, a perfluoroalkane, a perfluoroether, or a perfluoroamine.

12. The method of claim 1 wherein the fluorous eluting fluid comprises at least 50% fluorine by molecular weight.

13. The method of claim 1 wherein the fluorous eluting fluid comprises at least 60% percent fluorine by molecular weight.

14. The method of claim 1 wherein the fluorous eluting fluid comprises at least one cosolvent.

15. The method of claim 14 wherein the at least one cosolvent is a polar fluorinated solvent, an amphiphile solvent, an organic solvent or water.

* * * * *